(12) United States Patent
Castan et al.

(10) Patent No.: US 7,910,133 B2
(45) Date of Patent: *Mar. 22, 2011

(54) ORAL PHARMACEUTICAL FORMULATION IN THE FORM OF AQUEOUS SUSPENSION OF MICROCAPSULES FOR MODIFIED RELEASE OF AMOXICILLIN

(75) Inventors: Catherine Castan, Olienas (FR); Florence Guimberteau, Montussan (FR); Rémi Meyrueix, Lyons (FR)

(73) Assignee: Flamel Technologies, Venissieux (FR)

( * ) Notice: Subject to any disclaimer, the term of this patent is extended or adjusted under 35 U.S.C. 154(b) by 724 days.

This patent is subject to a terminal disclaimer.

(21) Appl. No.: 10/510,621

(22) PCT Filed: Apr. 7, 2003

(86) PCT No.: PCT/FR03/01095
§ 371 (c)(1),
(2), (4) Date: Oct. 6, 2005

(87) PCT Pub. No.: WO03/084517
PCT Pub. Date: Oct. 16, 2003

(65) Prior Publication Data
US 2006/0110463 A1    May 25, 2006

(30) Foreign Application Priority Data

Apr. 9, 2002 (FR) .................................. 02 04409
Sep. 2, 2002 (FR) .................................. 02 10846

(51) Int. Cl.
*A61K 9/14* (2006.01)
*A61K 9/16* (2006.01)
*A61K 9/40* (2006.01)
(52) U.S. Cl. ........ 424/489; 424/478; 424/490; 424/494; 424/497; 424/498

(58) Field of Classification Search .................. None
See application file for complete search history.

(56) References Cited

U.S. PATENT DOCUMENTS 3,864,483 A    2/1975  Stein et al.
3,892,769 A    7/1975  Shen et al.
(Continued)

FOREIGN PATENT DOCUMENTS

CA    2068366    11/1992
(Continued)

OTHER PUBLICATIONS

In the U.S. Patent and Trademark Office, Non-Final Office Action in re: U.S. Appl. No. 10/996,780, dated Dec. 12, 2008, 18 pages.

(Continued)

*Primary Examiner* — Juliet C Switzer
*Assistant Examiner* — Caralynne Helm
(74) *Attorney, Agent, or Firm* — Patton Boggs LLP

(57) ABSTRACT

The invention relates to liquid pharmaceutical formulations for oral administration with the modified release of amoxicillin, said formulations consisting of suspensions of coated particles of amoxicillin (microcapsules). According to the invention, the microcapsules constituting the disperse phase of the suspension are designed to allow the modified release of the amoxicillin according to a profile that does not change during the storage of the liquid suspension. To do this the inventors propose the selection of a specific coating composition for the microcapsules which consists of at least four components that allow these microcapsules to be stored in water without modifying their properties of modified release of the amoxicillin, this liquid phase furthermore being saturated with amoxicillin.

24 Claims, 2 Drawing Sheets

U.S. PATENT DOCUMENTS

| | | | |
|---|---|---|---|
| 3,914,414 A | 10/1975 | Stein et al. | |
| 3,914,415 A | 10/1975 | Stein et al. | |
| 3,927,216 A | 12/1975 | Witkowski et al. | |
| 3,966,917 A | 6/1976 | Prasad et al. | |
| 3,980,766 A | 9/1976 | Shaw et al. | |
| 4,029,884 A | 6/1977 | Stein et al. | |
| 4,070,494 A | 1/1978 | Hoffmeister et al. | |
| 4,308,251 A | 12/1981 | Dunn et al. | |
| 4,321,253 A * | 3/1982 | Beatty | 424/495 |
| 4,351,337 A | 9/1982 | Sidman | |
| 4,434,153 A | 2/1984 | Urquhart et al. | |
| 4,443,549 A | 4/1984 | Sadowski | |
| 4,450,150 A | 5/1984 | Sidman | |
| 4,454,309 A | 6/1984 | Gould et al. | |
| 4,461,759 A | 7/1984 | Dunn | |
| 4,486,471 A | 12/1984 | Samejima et al. | |
| 4,572,912 A | 2/1986 | Yoshioka et al. | |
| 4,639,436 A | 1/1987 | Junge et al. | |
| 4,693,896 A | 9/1987 | Wheatley et al. | |
| 4,728,512 A | 3/1988 | Mehta et al. | |
| 4,748,023 A | 5/1988 | Tamás et al. | |
| 4,833,905 A | 5/1989 | Hill | |
| 4,892,738 A | 1/1990 | Takagishi et al. | |
| 4,894,240 A | 1/1990 | Geoghegan et al. | |
| 4,902,513 A * | 2/1990 | Carvais | 424/455 |
| 4,904,769 A | 2/1990 | Rauenbusch | |
| 4,952,402 A | 8/1990 | Sparks et al. | |
| 4,999,189 A | 3/1991 | Kogan et al. | |
| 5,028,434 A | 7/1991 | Barclay et al. | |
| 5,045,321 A | 9/1991 | Makino et al. | |
| 5,084,278 A | 1/1992 | Mehta | |
| 5,091,485 A | 2/1992 | Noireaux et al. | |
| 5,158,636 A | 10/1992 | Groitzsch et al. | |
| 5,186,930 A | 2/1993 | Kogan et al. | |
| 5,206,030 A | 4/1993 | Wheatley et al. | |
| 5,219,895 A | 6/1993 | Kelman et al. | |
| 5,248,516 A | 9/1993 | Wheatley et al. | |
| 5,268,182 A | 12/1993 | Brinker et al. | |
| 5,286,495 A | 2/1994 | Batich et al. | |
| 5,286,497 A | 2/1994 | Hendrickson et al. | |
| 5,409,709 A | 4/1995 | Ozawa et al. | |
| 5,409,711 A | 4/1995 | Mapelli et al. | |
| 5,431,922 A | 7/1995 | Nicklasson | |
| 5,445,829 A | 8/1995 | Paradissis et al. | |
| 5,449,513 A | 9/1995 | Yokoyama et al. | |
| 5,464,632 A | 11/1995 | Cousin et al. | |
| 5,464,807 A | 11/1995 | Claude et al. | |
| 5,472,704 A | 12/1995 | Santus et al. | |
| 5,510,103 A | 4/1996 | Yokoyama et al. | |
| 5,571,533 A | 11/1996 | Santus et al. | |
| 5,589,455 A | 12/1996 | Woo | |
| 5,594,016 A | 1/1997 | Ueno et al. | |
| 5,603,957 A | 2/1997 | Burguiere et al. | |
| 5,609,872 A | 3/1997 | Ahlborg et al. | |
| 5,651,990 A | 7/1997 | Takada et al. | |
| 5,656,295 A | 8/1997 | Oshlack et al. | |
| 5,674,529 A | 10/1997 | Marder et al. | |
| 5,750,468 A | 5/1998 | Wright et al. | |
| 5,780,055 A | 7/1998 | Habib et al. | |
| 5,780,579 A | 7/1998 | Soula et al. | |
| 5,804,573 A | 9/1998 | Silver | |
| 5,846,566 A | 12/1998 | Burguiere et al. | |
| 5,858,398 A | 1/1999 | Cho | |
| 5,904,936 A | 5/1999 | Huille et al. | |
| 5,922,769 A | 7/1999 | Barelli et al. | |
| 5,945,123 A | 8/1999 | Hermelin | |
| 5,981,761 A | 11/1999 | Chou et al. | |
| 6,022,562 A * | 2/2000 | Autant et al. | 424/489 |
| 6,033,687 A | 3/2000 | Heinicke et al. | |
| 6,068,859 A | 5/2000 | Curatolo et al. | |
| 6,077,544 A | 6/2000 | Debregeas et al. | |
| 6,099,862 A | 8/2000 | Chen et al. | |
| 6,180,141 B1 | 1/2001 | Lemercier et al. | |
| 6,184,220 B1 * | 2/2001 | Turck et al. | 514/226.5 |
| 6,228,398 B1 | 5/2001 | Devane et al. | |
| 6,248,359 B1 | 6/2001 | Faour | |
| 6,264,983 B1 | 7/2001 | Upadhyay | |
| 6,274,173 B1 | 8/2001 | Sachs et al. | |
| 6,303,146 B1 | 10/2001 | Bonhomme et al. | |
| 6,309,663 B1 | 10/2001 | Patel et al. | |
| 6,309,668 B1 | 10/2001 | Bastin et al. | |
| 6,419,960 B1 | 7/2002 | Krishnamurthy et al. | |
| 6,472,373 B1 | 10/2002 | Albrecht | |
| 6,475,521 B1 | 11/2002 | Timmins et al. | |
| 6,627,635 B2 | 9/2003 | Palermo et al. | |
| 6,630,171 B1 | 10/2003 | Huille et al. | |
| 6,671,904 B2 | 1/2004 | Easterling | |
| 6,692,768 B1 | 2/2004 | Ishibashi et al. | |
| 6,696,088 B2 | 2/2004 | Oshlack et al. | |
| 6,699,506 B1 * | 3/2004 | Paillard et al. | 424/489 |
| 6,815,542 B2 | 11/2004 | Hong et al. | |
| 6,846,810 B2 | 1/2005 | Martin et al. | |
| 6,903,079 B2 | 6/2005 | Jagtap et al. | |
| 6,946,146 B2 | 9/2005 | Mulye | |
| 7,022,345 B2 | 4/2006 | Valducci | |
| 2001/0000510 A1 | 4/2001 | Sakurai et al. | |
| 2001/0006650 A1 | 7/2001 | Burnside et al. | |
| 2002/0068085 A1 | 6/2002 | Rudnic et al. | |
| 2002/0197327 A1 * | 12/2002 | Ulrich et al. | 424/497 |
| 2003/0050620 A1 | 3/2003 | Odidi et al. | |
| 2003/0064108 A1 | 4/2003 | Lukas et al. | |
| 2003/0068371 A1 | 4/2003 | Oshlack et al. | |
| 2003/0077297 A1 | 4/2003 | Chen et al. | |
| 2003/0099711 A1 * | 5/2003 | Meadows et al. | 424/474 |
| 2003/0104052 A1 | 6/2003 | Berner et al. | |
| 2003/0104056 A1 | 6/2003 | Rudnic et al. | |
| 2003/0118641 A1 | 6/2003 | Maloney et al. | |
| 2003/0220399 A1 | 11/2003 | Luskey et al. | |
| 2003/0224051 A1 | 12/2003 | Fink et al. | |
| 2004/0022849 A1 | 2/2004 | Castan et al. | |
| 2004/0121015 A1 | 6/2004 | Chidlaw et al. | |
| 2004/0121676 A1 | 6/2004 | Seko et al. | |
| 2004/0126428 A1 | 7/2004 | Hughes et al. | |
| 2004/0171584 A1 | 9/2004 | Millan et al. | |
| 2004/0228924 A1 | 11/2004 | Oshlack et al. | |
| 2004/0234601 A1 | 11/2004 | Legrand et al. | |
| 2005/0019406 A1 | 1/2005 | Kerrish et al. | |
| 2005/0037077 A1 * | 2/2005 | Legrand et al. | 424/469 |
| 2005/0059667 A1 | 3/2005 | Wolff | |
| 2005/0089572 A1 | 4/2005 | Kumar et al. | |
| 2005/0106249 A1 | 5/2005 | Hwang et al. | |
| 2005/0158392 A1 | 7/2005 | Kim et al. | |
| 2005/0163856 A1 | 7/2005 | Maloney et al. | |
| 2005/0281748 A1 | 12/2005 | Hirsh et al. | |
| 2006/0099264 A1 | 5/2006 | Chan et al. | |
| 2006/0165809 A1 * | 7/2006 | Guimberteau et al. | 424/490 |
| 2007/0173464 A1 | 7/2007 | Guimberteau et al. | |
| 2007/0196497 A1 | 8/2007 | Pouliquen et al. | |
| 2008/0020018 A1 | 1/2008 | Moodley et al. | |

FOREIGN PATENT DOCUMENTS

| | | |
|---|---|---|
| DE | 2 213 180 | 9/1972 |
| DE | 3 943 242 | 6/1990 |
| EP | 0 005 129 | 10/1979 |
| EP | 0 103 991 | 3/1984 |
| EP | 0 166 287 | 1/1986 |
| EP | 0 174 726 | 3/1986 |
| EP | 0 179 023 | 4/1986 |
| EP | 0 198 769 | 10/1986 |
| EP | 0 202 051 | 11/1986 |
| EP | 0 207 041 | 12/1986 |
| EP | 0 213 563 | 3/1987 |
| EP | 0 239 361 | 9/1987 |
| EP | 0 249 587 | 12/1987 |
| EP | 0 263 083 | 4/1988 |
| EP | 0 273 890 | 7/1988 |
| EP | 0 281 200 | 9/1988 |
| EP | 0 383 967 | 8/1990 |
| EP | 0 391 518 | 10/1990 |
| EP | 0 411 590 | 2/1991 |
| EP | 0 413 120 | 2/1991 |
| EP | 0 475 536 | 3/1992 |
| EP | 0 475 536 A1 | 3/1992 |
| EP | 0 624 371 | 11/1994 |
| EP | 0 647 448 | 4/1995 |
| EP | 0 709 087 | 5/1996 |
| EP | 0 721 776 | 7/1996 |

| | | |
|---|---|---|
| EP | 0 734 720 | 10/1996 |
| EP | 0 793 959 | 9/1997 |
| EP | 0 953 350 | 11/1999 |
| EP | 0 953 359 | 11/1999 |
| EP | 0 974 356 | 1/2000 |
| EP | 1 062 955 A1 | 12/2000 |
| EP | 1 086 694 | 3/2001 |
| EP | 1 101 490 | 5/2001 |
| EP | 1 123 700 A1 | 8/2001 |
| EP | 1 293 209 | 3/2003 |
| EP | 1 391 994 | 2/2004 |
| FR | 2 313 915 | 1/1977 |
| FR | 2 634 377 | 1/1990 |
| FR | 2 670 112 | 6/1992 |
| FR | 2 746 035 | 9/1997 |
| FR | 2 759 083 | 8/1998 |
| FR | 2 801 226 | 5/2001 |
| FR | 2 811 571 | 1/2002 |
| FR | 2 816 840 | 5/2002 |
| FR | 2 830 447 | 4/2003 |
| FR | 2 837 100 | 9/2003 |
| FR | 2 840 614 | 12/2003 |
| FR | 2 842 736 | 1/2004 |
| FR | 2 843 117 | 2/2004 |
| GB | 2 163 747 | 3/1986 |
| GB | 2 202 143 | 9/1988 |
| JP | 61-109711 | 5/1986 |
| JP | 63-301816 | 12/1988 |
| JP | 8-073345 | 3/1996 |
| JP | 10-324643 | 12/1998 |
| JP | 11-269064 | 10/1999 |
| JP | 11-322588 | 11/1999 |
| JP | 2000-256182 | 9/2000 |
| WO | WO 87/07833 | 12/1987 |
| WO | WO 88/01213 | 2/1988 |
| WO | WO 89/08449 | 9/1989 |
| WO | WO 91/06286 | 5/1991 |
| WO | WO 91/06287 | 5/1991 |
| WO | WO 91/19711 | 12/1991 |
| WO | WO 91/19712 | 12/1991 |
| WO | WO 92/01446 | 2/1992 |
| WO | WO 93/01805 | 2/1993 |
| WO | WO 94/09762 | 5/1994 |
| WO | WO 94/27988 | 12/1994 |
| WO | WO 96/01628 | 1/1996 |
| WO | WO 96/08243 | 3/1996 |
| WO | WO 96/08277 | 3/1996 |
| WO | WO 96/11675 | 4/1996 |
| WO | WO 96/29991 | 10/1996 |
| WO | WO 97/02810 | 1/1997 |
| WO | WO 97/09042 | 3/1997 |
| WO | WO 97/21436 | 6/1997 |
| WO | WO 97/25066 | 7/1997 |
| WO | WO 97/34584 | 9/1997 |
| WO | WO 98/24411 | 6/1998 |
| WO | WO 98/42311 | 10/1998 |
| WO | WO 98/53680 | 12/1998 |
| WO | WO 98/55107 | 12/1998 |
| WO | WO 99/26608 | 6/1999 |
| WO | WO 99/32091 | 7/1999 |
| WO | WO 99/47125 | 9/1999 |
| WO | WO 99/47128 | 9/1999 |
| WO | WO 99/49846 | 10/1999 |
| WO | WO 00/018374 | 4/2000 |
| WO | WO 00/028989 | 5/2000 |
| WO | WO 00/040233 | 7/2000 |
| WO | WO 00/050015 | 8/2000 |
| WO | WO 00/061116 | 10/2000 |
| WO | WO 00/078293 | 12/2000 |
| WO | WO 01/08661 | 2/2001 |
| WO | WO 01/021159 | 3/2001 |
| WO | WO 01/032157 | 5/2001 |
| WO | WO 01/032158 | 5/2001 |
| WO | WO 01/037809 | 5/2001 |
| WO | WO 01/058424 | 8/2001 |
| WO | WO 02/039984 | 5/2002 |
| WO | WO 02/053097 | 7/2002 |
| WO | WO02/066002 | 8/2002 |
| WO | WO 02/072072 | 9/2002 |
| WO | WO 02/094285 | 11/2002 |
| WO | WO 03/013479 | 2/2003 |
| WO | WO 2003/013467 | 2/2003 |
| WO | WO 03/020243 | 3/2003 |
| WO | WO 03/033001 | 4/2003 |
| WO | WO 2003/030878 | 4/2003 |
| WO | WO 03/035029 | 5/2003 |
| WO | WO 03/035039 | 5/2003 |
| WO | WO 03/077888 | 9/2003 |
| WO | WO 03/084517 | 10/2003 |
| WO | WO 03/084518 | 10/2003 |
| WO | WO 2003/082204 | 10/2003 |
| WO | WO 03/094899 | 11/2003 |
| WO | WO 03/094924 | 11/2003 |
| WO | WO 2004/004693 | 1/2004 |
| WO | WO 2004/010983 | 2/2004 |
| WO | WO 2004/010984 | 2/2004 |
| WO | WO 2004/026262 | 4/2004 |
| WO | WO 2004/035020 | 4/2004 |
| WO | WO 2004/035090 | 4/2004 |
| WO | WO 2004/052346 | 6/2004 |
| WO | WO 2004/054542 | 7/2004 |
| WO | WO 2004/056337 | 7/2004 |
| WO | WO 2004/064834 | 8/2004 |
| WO | WO 2004/087175 | 10/2004 |
| WO | WO 2005/016313 | 2/2005 |
| WO | WO 2005/016314 | 2/2005 |
| WO | WO 2005/016370 | 2/2005 |
| WO | WO 2005/079760 | 9/2005 |
| WO | WO 2006/056712 | 6/2006 |
| WO | WO 2006/056713 | 6/2006 |
| WO | WO 2006/089843 | 8/2006 |
| WO | WO 2006/125819 | 11/2006 |
| WO | WO 2006/133733 | 12/2006 |
| WO | WO 2006/134018 | 12/2006 |
| WO | WO 2007/054378 | 5/2007 |
| WO | WO 2007/093642 | 8/2007 |

OTHER PUBLICATIONS

In the U.S. Patent and Trademark Office, Non-Final Office Action in re: U.S. Appl. No. 11/439,432, dated Jan. 30, 2009, 22 pages.
In the U.S. Patent and Trademark Office, Non-Final Office Action in re: U.S. Appl. No. 10/398,134, dated May 12, 2005, 8 pages.
In the U.S. Patent and Trademark Office, Non-Final Office Action in re: U.S. Appl. No. 10/398,134, dated Jan. 18, 2006, 10 pages.
In the U.S. Patent and Trademark Office, Final Office Action in re: U.S. Appl. No. 10/398,134, dated Oct. 17, 2006, 4 pages.
In the U.S. Patent and Trademark Office, Non-Final Office Action in re: U.S. Appl. No. 10/332,463, dated Dec. 23, 2005, 6 pages.
In the U.S. Patent and Trademark Office, Final Office Action in re: U.S. Appl. No. 10/332,463, dated Sep. 21, 2006, 11 pages.
In the U.S. Patent and Trademark Office, Non-Final Office Action in re: U.S. Appl. No. 11/723,553, dated Oct. 4, 2007, 7 pages.
In the U.S. Patent and Trademark Office, Final Office Action in re: U.S. Appl. No. 11/723,553, dated Aug. 26, 2008, 11 pages.
In the U.S. Patent and Trademark Office, Non-Final Office Action in re: U.S. Appl. No. 10/415,850, dated Mar. 28, 2006, 14 pages.
In the U.S. Patent and Trademark Office, Non-Final Office Action in re: U.S. Appl. No. 10/415,850, dated Feb. 18, 2009, 7 pages.
In the U.S. Patent and Trademark Office, Final Office Action in re: U.S. Appl. No. 10/415,850, dated Aug. 18, 2009, 8 pages.
In the U.S. Patent and Trademark Office, Non-Final Office Action in re: U.S. Appl. No. 10/492,129, dated Jul. 26, 2007, 10 pages.
In the U.S. Patent and Trademark Office, Non-Final Office Action in re: U.S. Appl. No. 10/492,129, dated Sep. 8, 2008, 11 pages.
In the U.S. Patent and Trademark Office, Non-Final Office Action in re: U.S. Appl. No. 10/492,129, dated Apr. 29, 2009, 13 pages.
In the U.S. Patent and Trademark Office, Non-Final Office Action in re: U.S. Appl. No. 10/826,690, dated Jul. 27, 2007, 13 pages.
In the U.S. Patent and Trademark Office, Final Office Action in re: U.S. Appl. No. 10/826,690, dated Jan. 7, 2009, 9 pages.
In the U.S. Patent and Trademark Office, Non-Final Office Action in re: U.S. Appl. No. 10/478,420, dated Sep. 30, 2008, 18 pages.
In the U.S. Patent and Trademark Office, Final Office Action in re: U.S. Appl. No. 10/478,420, dated Jul. 1, 2009, 27 pages.

In the U.S. Patent and Trademark Office, Non-Final Office Action in re: U.S. Appl. No. 10/507,886, dated Jul. 21, 2009, 11 pages.
In the U.S. Patent and Trademark Office, Non-Final Office Action in re: U.S. Appl. No. 10/510,643, dated Feb. 5, 2008, 14 pages.
In the U.S. Patent and Trademark Office, Final Office Action in re: U.S. Appl. No. 10/510,643, dated Mar. 25, 2009, 19 pages.
In the U.S. Patent and Trademark Office, Non-Final Office Action in re: U.S. Appl. No. 10/522,252, dated Jan. 14, 2008, 10 pages.
In the U.S. Patent and Trademark Office, Final Office Action in re: U.S. Appl. No. 10/522,252, dated Aug. 19, 2008, 11 pages.
In the U.S. Patent and Trademark Office, Non-Final Office Action in re: U.S. Appl. No. 10/522,252, dated Jul. 6, 2009, 12 pages.
In the U.S. Patent and Trademark Office, Non-Final Office Action in re: U.S. Appl. No. 11/583,940, dated Mar. 3, 2008, 9 pages.
In the U.S. Patent and Trademark Office, Final Office Action in re: U.S. Appl. No. 11/583,940, dated Feb. 4, 2009, 13 pages.
In the U.S. Patent and Trademark Office, Non-Final Office Action in re: U.S. Appl. No. 11/583,940, dated Sep. 2, 2009, 11 pages.
In the U.S. Patent and Trademark Office, Non-Final Office Action in re: U.S. Appl. No. 10/522,234, dated Jan. 14, 2008, 11 pages.
In the U.S. Patent and Trademark Office, Non-Final Office Action in re: U.S. Appl. No. 11/802,610, dated Apr. 16, 2009, 9 pages.
In the U.S. Patent and Trademark Office, Non-Final Office Action in re: U.S. Appl. No. 11/648,605, dated Apr. 15, 2009, 15 pages.
In the U.S. Patent and Trademark Office, Non-Final Office Action in re: U.S. Appl. No. 11/651,577, dated Dec. 26, 2008, 23 pages.
In the U.S. Patent and Trademark Office, Final Office Action in re: U.S. Appl. No. 11/651,577, dated Jul. 31, 2009, 8 pages.
In the U.S. Patent and Trademark Office, Non-Final Office Action in re: U.S. Appl. No. 11/631,030, dated May 12, 2009, 5 pages.
"Product Information, Losartan (potassium salt)," *Cayman Chemical*, 2005; p. 1.
Akiyoshi et al., "Stabilization of Insulin upon Supramolecular Complexation with Hydrophobized Polysaccharide Nanoparticle," *Chemistry Letters*, 1995; 8:707-08.
Amidon et al., "A Theoretical Basis for a Biopharmaceutic Drug Classification: The Correlation of in vitro Drug Product Dissolution and in vivo Bioavailability," *Pharmaceutical Research*, 1995; 12(3):413-420.
Becker et al., "Current Approaches to Prevent NSAID-Induced Gastropathy—COX Selectivity and Beyond," *British Journal of Clinical Pharmacology*, 2004; 58(6):587-600.
Candau, S., "Chapter 3: Light Scattering," *Surfactant Solutions*, vol. 22, Ed. R. Zana, M. Dekker, Inc., NY, 1984; pp. 147-207.
Catella-Lawson et al., "Cyclooxygenase Inhibitors and the Antiplatelet Effects of Aspirin," *New England Journal of Medicine*, 2001; 345(25):1809-17.
Committee for Proprietary Medicinal Products, "Note for Guidance on Quality of Modified Release Products: A: Oral Dosage Forms, B: Transdermal Dosage Forms, Section 1 (Quality),"*The European Agency for the Evaluation of Medicinal Products—Human Medicines Evaluation Unit*, CPMP/QWP/604/96, 1999; pp. 1-5.

Constancis et al., "Macromolecular Colloids of Diblock Poly(amino acids) that Bind Insulin," *Journal of Colloid and Interface Science*, 1999; 217:357-368.
Davis et al., "The design and evaluation of controlled release systems for the gastrointestinal tract", *J. Controlled Release*, 1985; 2:27-38.
Fuller, W.D., "A procedure for the facile synthesis of amino-acid n-carboxyanhydrides," *Biopolymers* , 1976;15:1869-71.
Gao et al., "Measurement of the Binding of Proteins to Polyelectrolytes by Frontal Analysis Continuous Capillary Electrophoresis," Anal. Chem., 1997; 69:2945-51.
Gavrilin et al., "A Comparative Study of the Pharmacokinetics and Bioaccessibility of Potassium Losartan in Various Medicinal Forms," *Pharmaceutical Chemistry Journal*, 2002; 36(5):227-28.
Harada et al., "Formation of Polyion Complex Micelles in an Aqueous Milieu from a Pair of Oppositely-Charged Block Copolymers with Poly(ethylene glycol) Segments," *Macromolecules*, 1995; 28:5294-99.
Humphrey, M.J., "The Oral Bioavailability of Peptides and Related Drugs," *Delivery System for Peptide Drugs*, Plenum Press, 1986, pp. 139-151.
Kataoka, K. "Preparation of Novel Drug Carrier based on the Self-Association of Block Copolymer," *Drug Delivery System*, 1995; 10(5):363-70.
Kawana et al., "Nucleoside Peptides. III. The Synthesis of N[1-(9-Adenyl)-β-D-ribofuranuronosyl] Derivatives of Certain Amino Acids and Peptides," *J. Org. Chem.*, 1972; 37:288-291.
Jen et al., "Ribavirin dosing in chronic hepatitis C: Application of population pharmacokinetic-pharmacodynamic models," *Clin. Phannacol. Ther.*, 2002; 72(4):349-361.
Qingshseng, "Release—Sustained Pellet of Ribavirin," XP002395861, 2004, *Chemical Abstracts*, Data Accession No. 2005:353828. (Abstract only).
Tao, X et al., "Preparation of Ribavirin Sustained—Release Pellets by Centrifugal Granulation Technology," XP002395860, 2005, *Chemical Abstracts*, Database accession No. 2005:500395. (Abstract only).
Torriani et al., "Peginterferon Alfa-2a plus Ribavirin for Chronic Hepatitis C Virus Infection in HIV-Infected Patients," *The New England Journal of Medicine*, 2004;351(5): 438-450.
Tsutsumiuchi et al., "Synthesis of Polyoxazoline-(Glyco)peptide Block Copolymer Ring- opening Polymerization of (Sugar-Substituted) α-Amino Acid N-Carboxyanhydrides with Polyoxazoline Macroinitiators," *Macromolecules*, 1997; 30:4013-17.
Uchida et al., "Preparation and Evaluation of Sustained Release of Ethyl Cellulose Microcapsules Containing Ampicillin or Amoxicillin Using Rabbits, Beagle Dogs and Humans," *J. Pharmacobio-Dyn.*, 1986; 9(5):13.
Yoshino, H., "Design and Evaluation of Time Controlled Release Systems for Site-Specific Oral Drug Delivery to the GI Tract," *Current Status on Targeted Drug Delivery to the GI Tract*, Capsugel Library, Symp. Ser. Short Hills 22/4, London 6/05, Tokyo 14/05, 1993; pp. 185-190.

\* cited by examiner

ORAL PHARMACEUTICAL FORMULATION IN THE FORM OF AQUEOUS SUSPENSION OF MICROCAPSULES FOR MODIFIED RELEASE OF AMOXICILLIN

The invention relates to the field of the modified release of pharmaceutical active principles. In the present disclosure, the expression "modified release" arbitrarily denotes release of the active principle(s) which starts as soon as the galenical form is brought into contact with its dissolution medium (in vivo or in vitro) or release of the active principle(s) which does not start until after a predetermined period ranging e.g. from 0.5 to several hours. In terms of the invention, the time taken to release 50% of the active principle(s) is typically several hours and can extend e.g. from 0.5 to 30 hours.

More precisely, the invention relates to liquid pharmaceutical formulations for oral administration with the modified release of amoxicillin (an antibiotic of the β-lactam family). These formulations consist of suspensions or dispersions of microcapsules, each of which is formed of a core comprising amoxicillin and of a coating enveloping said core. According to the invention, the microcapsules constituting the disperse phase of the suspension are designed to allow the modified release of the amoxicillin.

The invention further relates to dry pharmaceutical formulations for use in aqueous suspensions reconstituted at the beginning of the treatment. These reconstituted aqueous suspensions are stable throughout the treatment and allow the modified release of the amoxicillin.

These suspensions are of particular value for
- increasing the interval between two dosage units, for example every 12 hours instead of every 8 hours;
- and facilitating the oral administration of an amoxicillin-based drug. In fact, a large number of patients would rather drink a liquid medicinal suspension than swallow one or more tablets. Compliance is thereby improved. This is of most particular value to populations incapable of swallowing tablets that are often large, namely infants, children and the elderly;
- while at the same time improving the taste of the suspension.

The invention further relates to a specific process for the preparation of microcapsules of amoxicillin to be suspended in water.

Numerous types of microcapsules in dry form are known. In particular, patent EP-B-0709 087 describes a (pharmaceutical or dietetic) galenical system, preferably in the form of a tablet, advantageously a disintegrating tablet, or in the form of a powder or gelatin capsule, characterized in that it comprises microcapsules of the reservoir type containing at least one medicinal and/or nutritional active principle (AP) selected especially from antibiotics, and intended for oral administration, characterized in that:
- they consist of particles of AP each covered with a film coating of the following composition:
  1—at least one film-forming polymer (P1) insoluble in the tract fluids, present in an amount of 50 to 90% by dry weight, based on the total weight of the coating composition, and consisting of at least one water-insoluble cellulose derivative, ethyl cellulose and/or cellulose acetate being particularly preferred;
  2—at least one nitrogen-containing polymer (P2) present in an amount of 2 to 25% by dry weight, based on the total weight of the coating composition, and consisting of at least one polyacrylamide and/or poly-N-vinylamide and/or poly-N-vinyllactam, polyacrylamide and/or polyvinylpyrrolidone being particularly preferred;
  3—at least one plasticizer present in an amount of 2 to 20% by dry weight, based on the total weight of the coating composition, and consisting of at least one of the following compounds: glycerol esters, phthalates, citrates, sebacates, cetyl alcohol esters, castor oil, salicylic acid and cutin, castor oil being particularly preferred;
  4—and at least one surfactant and/or lubricant present in an amount of 2 to 20% by dry weight, based on the total weight of the coating composition, and selected from anionic surfactants, preferably alkali metal or alkaline earth metal salts of fatty acids, stearic and/or oleic acid being preferred, and/or from non-ionic surfactants, preferably polyethoxylated sorbitan esters and/or polyethoxylated castor oil derivatives, and/or from lubricants such as stearates, preferably calcium, magnesium, aluminium or zinc stearate, or stearylfumarate, preferably sodium stearylfumarate, and/or glycerol behenate, it being possible for said agent to comprise only one or a mixture of the above-mentioned products;
- they have a particle size of between 50 and 1000 microns;
- and they are designed so as to be able to reside in the small intestine for a period of at least about 5 hours, thereby allowing the absorption of the AP during at least part of their residence time in the small intestine.

Said document relates only to dry pharmaceutical forms based on microcapsules and makes no mention of oral liquid pharmaceutical forms based on microcapsules.

Oral pharmaceutical formulations for the modified release of amoxicillin currently exist only in the form of tablets. Patents WO-A-94/27557, WO-A-95/20946, WO-A-95/28148, WO-A-96/04908, WO-A-00/61115, WO-A-00/61116, WO-A-01/47499 and WO-A-02/30392 describe different formulations of such tablets. These tablets are large, such as the tablet of Example 1 of patent WO 02/30392, which has a total weight of 1600 mg for a dose of 1000 g. These tablets cannot be administered to patients with swallowing difficulties, and even less to children or infants, who in any case are incapable of swallowing them and for whom, in addition, the dose administered has to be adapted according to their weight.

For such applications, multidose suspensions or solutions are preferable to tablets as pharmaceutical forms.

Pharmaceutical suspensions or solutions of amoxicillin exist to meet this need. Examples of these are the formulations described by patent application WO-A-98/35672 or WO-A-98/35672. Efforts to improve these suspensions have been directed towards suspension stability (patent application WO-A-00/50036), gastrointestinal tolerance (patent applications WO-A-97/06798 & WO-A-00/03695) or taste improvement (patent application WO-A-98/36732).

However, none of these known suspensions allows the modified release of amoxicillin, which is necessary to increase the duration of action of the amoxicillin and treat certain indications such as pneumonia caused by resistant streptococci. To meet this need, a formulation containing more than the customary amount of amoxicillin is described in patent application WO-A-97/09042, in which the amoxicillin is in an immediate-release form.

Liquid suspensions for the modified release of amoxicillin are difficult to produce. The main difficulty to be overcome is that of avoiding the release of the amoxicillin into the liquid phase during storage of the suspension, while allowing modified release as soon as it enters the gastrointestinal tract. This objective is particularly difficult to achieve because the amoxicillin is stored in a liquid for a very long time (the duration of the treatment, i.e. about ten days) compared with the desired release time in the gastrointestinal tract fluids (a few hours, at most 12). Furthermore, its prolonged residence in the liquid phase during storage must not perturb the modified-release system to the point of degrading the release profile and release time of the amoxicillin.

Furthermore, for these liquid formulations to be fully effective, it is known to be important that:

the microcapsules are very small (<1000 microns), and the weight fraction of coating excipients is limited, this modality being all the more difficult to achieve because, due to their small size, the microcapsules have a large specific surface area, accelerating the release.

As regards the prior art concerning oral liquid pharmaceutical forms for the modified release of active principles, PCT patent application WO-A-87/07833 and U.S. Pat. No. 4,902,513 should be mentioned first of all; . . . disclose aqueous suspensions of microcapsules of active principle (e.g. theophylline) with modified release of the active principle (e.g. 12 h). These suspensions are prepared by saturating the aqueous phase with the active principle before incorporating the microcapsules of active principle into this aqueous phase. The composition of the coating agent for the microcapsules that allows the modified release of the active principle is not described in said documents. Now, this coating composition is a decisive factor in guaranteeing the maintenance of the modified-release profile of the microcapsules after storage in the aqueous phase. The technical proposal described appears not to disclose the means of solving the dual problem of producing a liquid suspension of a modified-release microcapsular form without interfering with the stability of the modified-release profile of the active principle after the microcapsules have been stored in the liquid phase.

European patent application EP-A-0 601 508 relates to an aqueous suspension for the oral administration of naxopren according to a modified-release profile. This suspension comprises coated microgranules of naxopren suspended in a syrupy aqueous liquid phase. The technical problem underlying this invention is to provide a modified-release form of naxopren containing a 1000 mg dose and capable of administration in a single daily dosage unit.

The microgranules consist of naxopren, polyvinylpyrrolidone and lactose (90-300 µm). Their coating is made up of 4 layers. The first comprises diethyl cellulose/diethyl phthalate/polyethylene glycol. The second is based on EUDRAGIT® (meth)acrylate/(meth)acrylic copolymers. The third comprises glycerol stearate/wax/fatty alcohols and the fourth consists of an enteric covering based on cellulose acetate/phthalate. The naxopren undergoes modified release over 24 hours.

Example 22 of said European patent application EP-A-0 601 508 contains a demonstration of the stability of the release profile after 30 days' storage of the liquid suspension.

One of the disadvantages of this suspension derives from the enteric layer, which prohibits the use of a suspension of neutral pH because this layer is designed to disintegrate and become liquid at neutral pH. Another disadvantage of this enteric layer is that it blocks the release of the active principle in the stomach at acidic pH. Now, amoxicillin, whose absorption window is situated in the upper parts of the gastrointestinal tract, must be released as soon as it reaches the stomach in order to be effectively absorbed. Furthermore, this multilayer solution to the problem is very complex and in addition specific to naproxen.

PCT patent application WO-A-96/01628 discloses a liquid pharmaceutical formulation for the oral administration, according to a modified-release profile (12 hours), of an active principle consisting of moguisteine. The object is to propose a modified-release liquid formulation of moguisteine which is easy to measure out and ingest, has a release time that makes it possible to avoid multiple dosage units, is stable over time in aqueous suspension and is pleasantly flavoured in order to favour compliance, and whose manufacture does not involve the use of toxic substances like solvents. To achieve this object, the invention according to PCT patent application WO-A-96/01628 proposes a suspension, in a weakly hydrated liquid phase (essentially based on sorbitol and glycerol), of microgranules (90-300 µm) of moguisteine coated with a first, hydrophilic layer consisting of cellulose acetate/phthalate and diethyl phthalate, a second, hydrophobic layer containing glycerol stearate/wax/fatty alcohols, and a third, hydrophilic layer identical to the first.

This multilayer form is very complex to prepare and in addition is specific to moguisteine.

In this state of the art, the essential objective of the present invention is to propose an aqueous suspension, or a preparation for an aqueous suspension, of microcapsules of amoxicillin for the oral administration of amoxicillin according to a modified-release profile, in which the coating of the microcapsules is designed in such a way that the release profile is not perturbed and does not depend on the maceration time of the microcapsules in the liquid (preferably aqueous) phase. Thus the amoxicillin contained in the microcapsules would be prevented from escaping into the liquid phase throughout the storage of the suspension, but a modified release of the amoxicillin would be allowed as soon as it entered an environment suitable for triggering the release, namely in vivo in the gastrointestinal tract and in vitro under the conditions of a dissolution test performed just after suspension of the microcapsules in the solvent (preferably aqueous) phase, using a type II apparatus according to the European Pharmacopoeia 3rd edition, in a phosphate buffer medium of pH 6.8, for a volume of 900 ml, at a temperature of 37° C.

Another objective of the present invention is to provide an aqueous liquid suspension of microcapsules of amoxicillin comprising a film coating formed of a single layer.

Another objective of the present invention is to provide an aqueous liquid suspension of microcapsules of amoxicillin in which the dissolved fraction originating from the microcapsules is less than or equal to 15% and preferably 5% of the total weight of amoxicillin present in the microcapsules.

Another objective of the present invention is to provide an aqueous liquid suspension of microcapsules of amoxicillin in which one part of the amoxicillin is in an immediate-release form and the other part of the amoxicillin is in a modified-release form (microcapsules).

Another essential objective of the present invention is to provide an aqueous suspension of microcapsules for the modified release of amoxicillin which makes it possible to release the amoxicillin according to a release profile that is not degraded by the ageing of the suspension.

Another essential objective of the present invention is to provide an aqueous suspension of microcapsules which is made up of individually coated particles of amoxicillin and makes it possible to release the latter according to a prolonged and/or optionally delayed profile such that the release half-life $t_{1/2}$ is between 0.5 and 30 hours.

Another objective of the present invention is to propose an oral galenical form which is liquid and consists of a large number (for example in the order of several thousands) of microcapsules, this multiplicity statistically ensuring a good reproducibility of the transit kinetics of the AP throughout the gastrointestinal tract, thereby improving control of the bioavailability and hence improving efficacy.

One essential objective of the present invention is to propose an oral liquid galenical form made up of a plurality of coated microcapsules which avoids the use of large amounts of coating agent, the weight fraction of coating agent being comparable to that of the monolithic forms.

Another essential objective of the present invention is to provide a modified-release aqueous suspension in which the amoxicillin is in the form of a plurality of particles individually coated to form microcapsules and allowing mixing with other active principles having different respective release times.

Another essential objective of the present invention is to propose the use, as a means of treating human or veterinary diseases, of a (preferably aqueous) suspension of microcapsules consisting of particles of amoxicillin individually coated so as to determine the modified release of the amoxicillin without the modified-release profile being affected by storage of the microcapsules in this liquid form in suspension.

Another essential objective of the present invention is to propose a drug based on a preferably aqueous suspension of microcapsules consisting of particles of amoxicillin individually coated so as to determine the modified release of the amoxicillin without the modified-release profile being affected by storage of the microcapsules in this liquid form in suspension.

Having set themselves all the above objectives, among others, the inventors have succeeded in developing a multi-microcapsular galenical system in the form of a preferably aqueous suspension for the modified release of amoxicillin which:

does not degrade the optionally retarded, modified-release profile, and is stable, easy to prepare, economic and effective.

To do this the inventors have proposed to:

select a totally specific coating composition for the microcapsules, and suspend the microcapsules in a (preferably aqueous) liquid phase saturated with amoxicillin or capable of being saturated with amoxicillin on contact with the microcapsules, using an amount of solvent (preferably water) that is limited but nevertheless sufficient for the suspension to be easy to swallow.

Thus the invention which meets the objectives described above, among others, relates to a suspension of microcapsules in an aqueous liquid phase, said suspension being intended for oral administration and allowing the modified release of amoxicillin, characterized in that:

it comprises a plurality of microcapsules each consisting of a core containing amoxicillin and of a film coating that:
is applied to the core,
controls the modified release of the amoxicillin,
and has a composition corresponding to one of the following three families A, B and C:
Family A
1A—at least one film-forming polymer (P1) insoluble in the tract fluids, present in an amount of 50 to 90 and preferably of 50 to 80% by dry weight, based on the total weight of the coating composition, and consisting of at least one water-insoluble cellulose derivative;
2A—at least one nitrogen-containing polymer (P2) present in an amount of 2 to 25 and preferably of 5 to 15% by dry weight, based on the total weight of the coating composition, and consisting of at least one polyacrylamide and/or poly-N-vinylamide and/or poly-N-vinyllactam;
3A—at least one plasticizer present in an amount of 2 to 20 and preferably of 4 to 15% by dry weight, based on the total weight of the coating composition, and consisting of at least one of the following compounds: glycerol esters, phthalates, citrates, sebacates, cetyl alcohol esters and castor oil;
4A—at least one surfactant and/or lubricant present in an amount of 2 to 20 and preferably of 4 to 15% by dry weight, based on the total weight of the coating composition, and selected from anionic surfactants and/or non-ionic surfactants and/or lubricants, it being possible for said agent to comprise only one or a mixture of the above-mentioned products;
Family B
1B—at least one hydrophilic polymer carrying groups ionized at neutral pH and preferably selected from cellulose derivatives;
2B—at least one hydrophobic compound different from A;
Family C
1C—at least one film-forming polymer insoluble in the gastrointestinal tract fluids;
2C—at least one water-soluble polymer;
3C—at least one plasticizer;
4C—optionally at least one surfactant/lubricant preferably selected from the following group of products:
anionic surfactants;
and/or non-ionic surfactants, and the liquid phase is saturated or becomes saturated with amoxicillin on contact with the microcapsules.

In terms of the present disclosure, the expression "microcapsules of amoxicillin" denotes microcapsules whose core comprises amoxicillin and optionally at least one other active principle and/or at least one excipient.

This suspension according to the invention makes it possible to overcome the two main obstacles to the production of an aqueous suspension of microcapsules consisting of individually coated microparticles of amoxicillin and allowing the modified release of the latter, these two obstacles being as follows:

a) limiting the fraction of amoxicillin immediately releasable from the microcapsules to a value of less than 15% and preferably 5% of the total weight of amoxicillin used in the microcapsules;

b) obtaining a modified-release system that is sufficiently robust to avoid any change or degradation of the release profile of the amoxicillin during storage of the aqueous suspension.

In one preferred embodiment of the invention, the families A, B and C from which the constituents of the coating composition are selected are as follows:
Family A
1A—ethyl cellulose and/or cellulose acetate;
2A—polyacrylamide and/or polyvinylpyrrolidone;
3A—castor oil;
4A—an alkali metal or alkaline earth metal salt of fatty acids, stearic and/or oleic acid being preferred, a polyethoxylated sorbitan ester, a polyethoxylated castor oil derivative, a stearate, preferably calcium, magnesium, aluminium or zinc stearate, a stearylfumarate, preferably sodium stearylfumarate, or glycerol behenate, taken individually or in a mixture with one another;

Family B
1B
cellulose acetate-phthalate;
hydroxypropyl methyl cellulose phthalate;
hydroxypropyl methyl cellulose acetate-succinate;
(meth)acrylic acid/(meth)acrylic acid alkyl (methyl) ester copolymer (EUDRAGIT® S or L);
and mixtures thereof;
2B
hydrogenated vegetable waxes (Dynasan® P60, Dynasan® 116);
triglycerides (tristearin, tripalmitin, Lubritab®, Cutina HR, etc.);
animal and vegetable fats (beeswax, carnauba wax, etc.);
and mixtures thereof.
Family C
1C
water-insoluble cellulose derivatives, ethyl cellulose and/or cellulose acetate being particularly preferred;
acrylic derivatives;
polyvinyl acetates;
and mixtures thereof;
2C
water-soluble cellulose derivatives;
polyacrylamides;
poly-N-vinylamides;
poly-N-vinyllactams;
polyvinyl alcohols (PVA);
polyoxyethylenes (POE);
polyvinylpyrrolidones (PVP) (the latter being preferred);
and mixtures thereof;
3C
glycerol and its esters, preferably from the following subgroup: acetylated glycerides, glycerol monostearate, glyceryl triacetate and glycerol tributyrate;
phthalates, preferably from the following subgroup: dibutyl phthalate, diethyl phthalate, dimethyl phthalate and dioctyl phthalate;
citrates, preferably from the following subgroup: acetyltributyl citrate, acetyltriethyl citrate, tributyl citrate and triethyl citrate;
sebacates, preferably from the following subgroup: diethyl sebacate and dibutyl sebacate;
adipates;
azelates;
benzoates;
vegetable oils;
fumarates, preferably diethyl fumarate;
malates, preferably diethyl malate;
oxalates, preferably diethyl oxalate;
succinates, preferably dibutyl succinate;
butyrates;
cetyl alcohol esters;
salicylic acid;
triacetin;
malonates, preferably diethyl malonate;
cutin;
castor oil (this being particularly preferred);
and mixtures thereof;
4C
alkali metal or alkaline earth metal salts of fatty acids, stearic and/or oleic acid being preferred;
polyethoxylated oils, preferably polyethoxylated hydrogenated castor oil;
polyoxyethylene/polyoxypropylene copolymers;
polyethoxylated sorbitan esters;
polyethoxylated castor oil derivatives;
stearates, preferably calcium, magnesium, aluminium or zinc stearate;
stearylfumarates, preferably sodium stearylfumarate;
glycerol behenate;
and mixtures thereof.

According to one advantageous modality of the invention in the case where the coating contains wax, the latter is selected from compounds whose melting point $T_f$ is $\geq 40°$ C. and preferably $\geq 50°$ C.

Preferably, the film coating consists of a single layer whose weight represents from 1 to 50% and preferably from 5 to 40% of the total weight of the microcapsules.

According to one preferred characteristic of the invention, the liquid phase is aqueous; even more preferably, it contains at least 20% of water and preferably at least 50% by weight of water.

This suspension according to the invention advantageously contains:
30 to 95% by weight and preferably 60 to 85% by weight of liquid phase (advantageously water);
and 5 to 70% by weight and preferably 15 to 40% by weight of microcapsules.

Advantageously, the amount of solvent liquid phase (preferably water) for the amoxicillin is such that the proportion of dissolved amoxicillin originating from the microcapsules is less than or equal to 15% and preferably less than or equal to 5% by weight, based on the total weight of amoxicillin contained in the microcapsules.

In a first embodiment of the invention, the liquid phase is at least partially and preferably totally saturated with amoxicillin following the incorporation of the microcapsules into this liquid phase.

In this embodiment, it is the amoxicillin contained in the microcapsules that saturates the liquid phase.

In a second embodiment of the invention, the liquid phase is at least partially and preferably totally saturated with amoxicillin by means of non-encapsulated amoxicillin prior to the incorporation of the microcapsules into this liquid phase. This embodiment is of particular value for the administration of amoxicillin in that it makes it possible to combine an immediate-release fraction with a modified-release fraction.

In practice, this amounts to saturating the liquid phase with amoxicillin before the introduction of the microcapsules into the suspension, so that the amoxicillin contained in the microcapsules plays no part, or virtually no part, in the saturation of the liquid phase. The diffusion of the amoxicillin contained in the microcapsules is therefore suppressed or virtually suppressed.

According to one preferred characteristic of the invention enabling this liquid oral formulation to be fully effective, the microcapsules have a particle size less than or equal to 1000 microns, preferably of between 200 and 800 microns and particularly preferably of between 200 and 600 microns.

"Particle size" is understood in terms of the invention as meaning that a proportion of at least 75% by weight of microcapsules have a diameter between the screen size limits in question.

Again with the aim of improving efficacy, the amount of coating agent for the microcapsules advantageously represents from 1 to 50% and preferably 5 to 40% of the weight of the coated microcapsules. This advantageous characteristic is all the . . . to acquire because, due to their small size, the microcapsules have a large specific surface area, accelerating the release.

To control the in vivo in vitro release of the amoxicillin, it is preferable according to the invention to use a film coating for the microcapsules which has a composition belonging to family A or C.

For more detailed qualitative and quantitative information on this coating composition of family A, reference may be made to European patent EP-B-0 709 087, the content of which forms part of the present disclosure by way of reference.

Another possible way of defining the liquid suspension according to the invention consists in considering an in vitro release profile obtained using a type II apparatus according to the European Pharmacopoeia 3rd edition, in a phosphate buffer medium of pH 6.8 and at a temperature of 37° C., such that:
the proportion PI of amoxicillin released from the microcapsules during the first 15 minutes of the dissolution test is such that:

$$PI \leq 15$$

preferably $PI \leq 5$;

the amoxicillin remaining in the microcapsules is released over a period such that the release time of 50% by weight of the amoxicillin ($t_{1/2}$) is defined as follows (in hours):

$$0.5 \leq t_{1/2} \leq 30$$

preferably $0.5 \leq t_{1/2} \leq 20$.

Still with regard to its in vitro dissolution properties, the suspension according to the invention is characterized in that:
the initial in vitro release profile Pfi obtained just after suspension of the microcapsules in the solvent (preferably aqueous) phase, using a type II apparatus according to the European Pharmacopoeia 3rd edition, in a phosphate buffer medium of pH 6.8, for a volume of 900 ml, at a temperature of 37° C.,
and the in vitro release profile $Pf_{10}$ obtained 10 days after suspension of the microcapsules in the solvent (preferably aqueous) phase, using a type II apparatus according to the European Pharmacopoeia 3rd edition, in a phosphate buffer medium of pH 6.8, at a temperature of 37° C.,
are similar.

The release profiles compared according to the recommendations of The European Agency for the Evaluation of Medicinal Products (EMEA)—Human Medicines Evaluation Unit—/Committee for proprietary medicinal products (CPMP)—London, 29 Jul. 1999, CPMP/QWP/604/96: note for guidance on quality of modified release products: A: oral dosage forms, B: transdermal dosage forms—section I (quality)—Annex 3: Similarity factor $f_2$, produce a value of >50 for the similarity factors $f_2$ and can therefore be declared similar.

These advantageous characteristics of the suspension according to the invention enable amoxicillin to be administered orally without difficulty and without detracting from the modified and optionally delayed release mode.

According to another of its advantageous physicochemical characteristics, the pH of the liquid suspension according to the invention can arbitrarily be acidic or neutral.

It may be quite valuable to add at least one rheology modifier to the suspension. In particular, this can be one or more "viscosifiers" selected . . . those commonly employed in the pharmaceutical industry and especially those disclosed in *Handbook of pharmaceutical excipients—3rd edition*, Am. Pharmaceutical Association, Arthur H. KIBBE, 2000, ISBN 0917330-96-X. Europe. 0-85369-381-1. Examples which may be mentioned are:

water-soluble cellulose derivatives (hydroxyethyl cellulose, hydroxypropyl cellulose, carboxymethyl cellulose, hydroxypropyl methyl cellulose, etc.);
polyethylene glycols;
alginates and derivatives thereof;
carrageenans;
agar-agar;
gelatin;
maltodextrins;
polydextrose;
guar, carob, acacia, xanthan, gellan and other gums;
polyvinyl alcohol;
povidone;
pectins;
silica gel;
native and modified starches and derivatives thereof;
dextrans;
etc.

It can also be advisable to introduce into the suspension at least one agent for modifying the solubility of the amoxicillin in the solvent (preferably aqueous) liquid phase, for example salts, sugars, glycerol, etc.

For the suspension to have all the qualities of an oral galenical form that is easy to swallow, stable and palatable, it advantageously contains at least one other additive selected from the group comprising surfactants, colourants, dispersants, preservatives, taste improvers, flavourings, sweeteners, antioxidants and mixtures thereof.

Examples of these additives which may be mentioned are those commonly employed in the pharmaceutical industry and especially those disclosed in *Handbook of pharmaceutical excipients—3rd edition*, Am. Pharmaceutical Association, Arthur H. KIBBE, 2000, ISBN 0917330-96-X. Europe. 0-85369-381-1, or, in the case of emulsifiers, those described on page 5, lines 14 to 29, of EP-A-0 273 890, or again, in the case of thickeners, those indicated on page 5, lines 19 and 20, of EP-A-0 601 508.

According to another of its features, the present invention relates to a drug, characterized in that it comprises a suspension of modified-release microcapsules of amoxicillin, as defined above.

In more concrete terms, the invention further relates to a drug, or more exactly a galenical pack, characterized in that it comprises a kit for preparing the suspension as defined above, said kit containing:
microcapsules in substantially dry form containing amoxicillin for saturating the liquid phase with amoxicillin once the two solid and liquid phases have been brought into contact;
and/or a mixture of microcapsules in substantially dry form containing amoxicillin in the dose that is just necessary for modified release, together with immediate-release uncoated amoxicillin in a necessary and sufficient amount to saturate the liquid phase with amoxicillin once the saturation dose of amoxicillin and the liquid phase have been brought into contact;
and the liquid phase and/or at least part of the ingredients useful for its preparation, and/or the protocol for preparation of the suspension.

This type of presentation of the drug according to the invention enables patients easily to prepare the modified-release suspension in a form that is stable, particularly in terms of modified release, for at least several days. The patient is thus guaranteed to have a drug that is easy to administer orally and perfectly effective from the therapeutic point of view.

The microcapsules constituting the solid phase of the suspension according to the invention can be prepared by microencapsulation techniques available to those skilled in the art, the main techniques being summarized in the article by C. DUVERNEY and J. P. BENOIT in "L'actualité chimique", December 1986. More precisely, the technique in question is microencapsulation by film coating, which yields individualized "reservoir" systems as opposed to matrix systems.

For further details, reference may be made to patent EP-B-0 953 359 cited above.

To produce the core based on amoxicillin of the microcapsules according to the invention, it is advantageous to use, as starting materials, particles of amoxicillin of the desired size. Said particles can be crystals of amoxicillin which are pure and/or have undergone a pretreatment by one of the techniques conventionally employed in the art, for example granulation, in the presence of a small amount of at least one conventional binder and/or an agent for modifying the intrinsic solubility characteristics of the amoxicillin.

The invention will be understood more clearly from the point of view of its composition, properties and preparation with the aid of the Examples below, given solely by way of illustration, which demonstrate the variants and the advantages of the invention.

Example 1

Preparation of Microcapsules of Amoxicillin 970 g of amoxicillin trihydrate and 30 g of povidone (Plasdone® K29/32) are first mixed dry in the bowl of a high-shear granulator (Lödige® M5MRK) for 5 minutes. This pulverulent mixture is then granulated with water (200 g). The granules are dried at 40° C. in a ventilated oven and then graded on a 500 µm screen. The 200-500 µm fraction is selected by sieving.

700 g of granules obtained above are coated in a GLATT GPCG1 fluidized air bed apparatus with 107.6 g of ethyl cellulose (Ethocel 7 Premium), 35.3 g of povidone (Plasdone® K29/32) and 10.8 g of castor oil dissolved in an acetone/isopropanol mixture (60/40 w/w).

Preparation of the Suspension:

12.2 g of microcapsules obtained above are mixed dry with 0.3 g of xanthan gum in a 100 ml glass flask. 87.5 g of purified water are then added to the powder mixture. After manual stirring, a suspension is obtained which produces a sediment very slowly. The amoxicillin titre in the suspension is 0.1 g/ml.

Stability Test:

The suspension prepared above is stored for 12 days at room temperature. After 12 days the suspension is analysed for dissolution using a type II apparatus according to the European Pharmacopoeia 3rd edition, phosphate buffer medium of pH 6.8, volume of 900 ml, temperature of 37° C., blade stirring at 100 rpm, UV detection at 272 nm.

Figure 1:
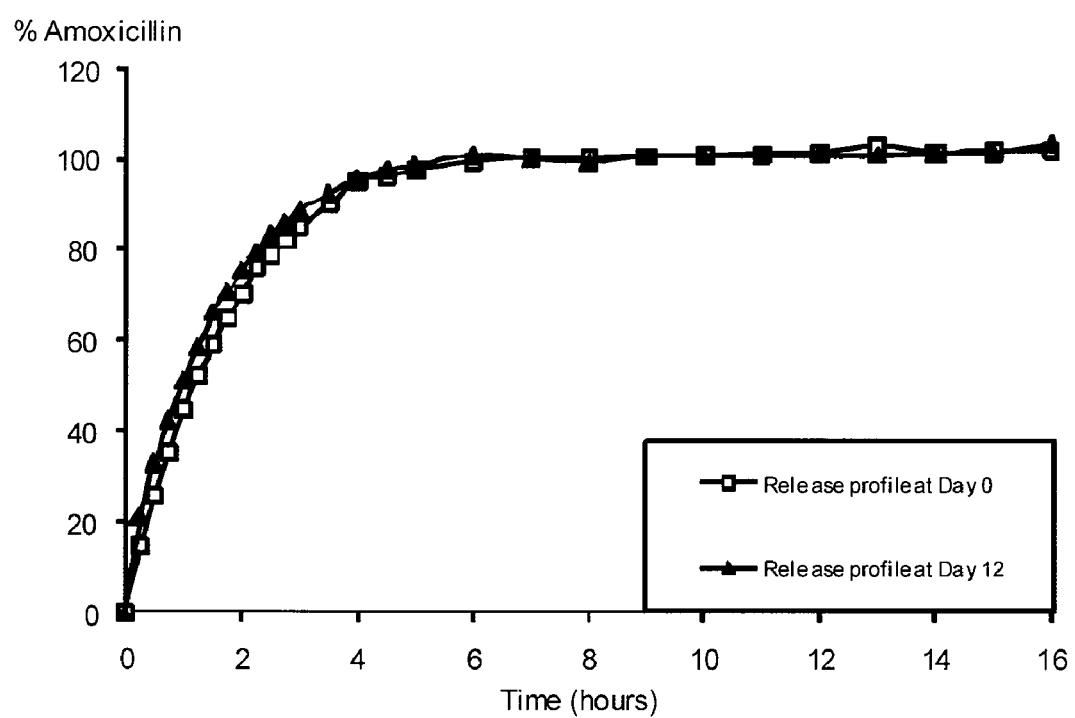
FIG. 1 shows the initial dissolution profile and the dissolution profile after 12 days' storage of the suspension according to Example 1, in % dissolved as a function of the time in hours.

The result is shown in FIG. 1 attached.

The profiles are apparently identical: similarity factor $f_2$ greater than 50. The microcapsules remain highly effective in aqueous suspension.

Homogeneity Test:

The above suspension is stirred manually and then six 5 ml samples are taken with a graduated syringe. The amoxicillin content of each sample is determined by HPLC and is shown below:

| Sample no. | Amoxicillin content for 5 ml of suspension (in g) |
| --- | --- |
| 1 | 0.51 |
| 2 | 0.49 |
| 3 | 0.52 |
| 4 | 0.50 |
| 5 | 0.50 |
| 6 | 0.51 |

It is seen that the samples are very homogeneous and that the dosage corresponds to the expected value of 0.5 g for 5 ml.

This formulation can therefore be administered without risk of overdosing or underdosing.

Example 2

Preparation of Microcapsules of Amoxicillin 970 g of amoxicillin trihydrate and 30 g of povidone (Plasdone® K29/32) are first mixed dry in the bowl of a high-shear granulator (Lödige® M5MRK) for 5 minutes. This pulverulent mixture is then granulated with water (200 g). The granules are dried at 40° C. in a ventilated oven and then graded on a 500 µm screen. The 200-500 µm fraction is selected by sieving.

920 g of granules obtained above are coated in a GLATT GPCG1 fluidized air bed apparatus with 61 g of Aquacoat ECD30, 2.6 g of povidone (Plasdone® K29/32) and 16.4 g of triethyl citrate dispersed in water.

Preparation of the Suspension:

10.9 g of microcapsules obtained above are mixed dry with 0.3 g of xanthan gum in a 100 ml glass flask. 88.8 g of purified water are then added to the powder mixture. After manual stirring, a suspension is obtained which produces a sediment very slowly.

The amoxicillin titre in the suspension is 0.1 g/ml.

Stability Test:

The suspension prepared above is stored for 12 days at room temperature. After 12 days the suspension is analysed for dissolution using a type II apparatus according to the European Pharmacopoeia 3rd edition, phosphate buffer medium of pH 6.8, volume of 900 ml, temperature of 37° C., blade stirring at 100 rpm, UV detection at 272 nm.

Figure 2:
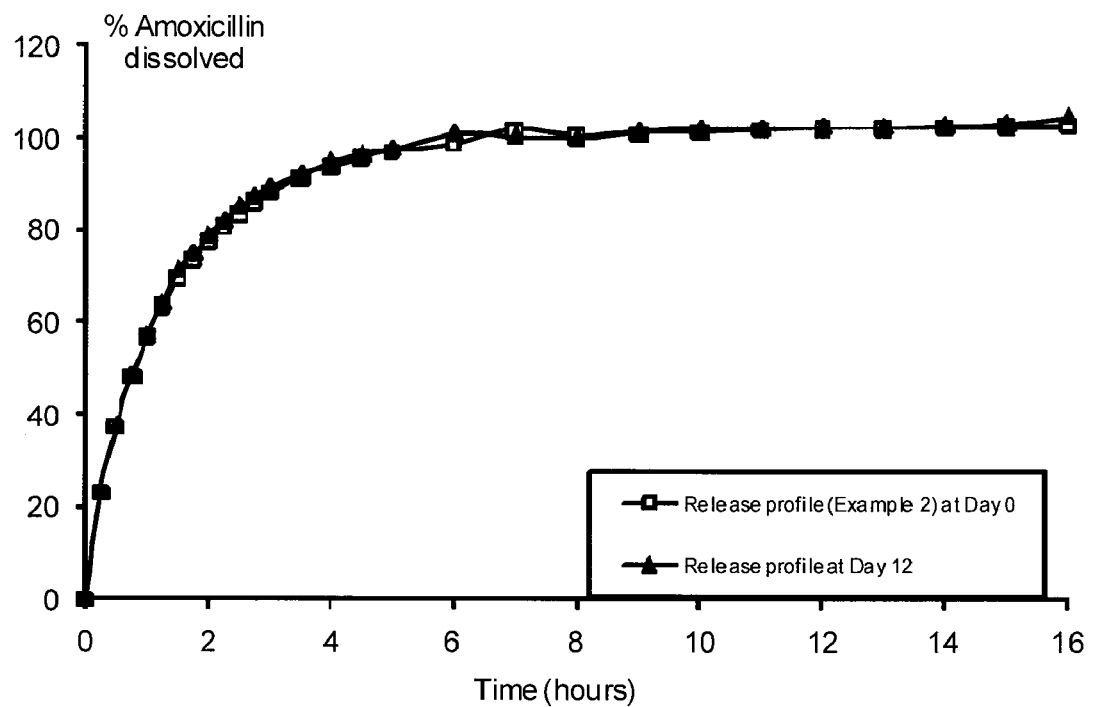
FIG. 2 shows the initial dissolution-profile and the dissolution profile after 12 days' storage of the suspension according to Example 2, in % dissolved as a function of the time in hours.

The result is shown in FIG. 2 attached.

The profiles are apparently identical: similarity factor $f_2$ greater than 50. The microcapsules remain highly effective in aqueous suspension.

KEY TO FIGURES

FIG. 1:
Amoxicilline=amoxicillin
Profil initial=Initial profile
Profil après 12 jours=Profile after 12 days FIG. 2:
Amoxicilline dissoute=amoxicillin dissolved
profil initial example 2=initial profile of Example 2
profil example 2 après 12 jours=profile of Example 2 after 12 days
Temps (heure)=Time (hours)

The invention claimed is:
1. A suspension of microcapsules in an aqueous liquid phase, said suspension being intended for oral administration and allowing the modified release of amoxicillin, wherein said suspension comprises a plurality of microcapsules and an aqueous liquid phase,
  wherein the aqueous liquid phase is saturated or becomes saturated with active principle(s) on contact with the microcapsules, and
  wherein each microcapsule comprises
    (a) a core comprising amoxicillin and
    (b) a film coating that: (i) is applied to the core, (ii) controls the modified release of the amoxicillin in gastrointestinal tract fluids, and (iii) comprises:
      (1) at least one film-forming polymer (P1) insoluble in gastrointestinal tract fluids, present in an amount of 50 to 90% by dry weight based on the total weight of the coating composition, and wherein at least one of said at least one film-forming polymer (P1) is a water-insoluble cellulose derivative;
      (2) at least one nitrogen-containing polymer (P2) present in an amount of 2 to 25% by dry weight based on the total weight of the coating composition, and wherein at least one of said at least one nitrogen-containing polymer (P2) is selected from the group consisting of: polyacrylamide, poly-N-vinylamide, and poly-N-vinyllactam; and
      (3) at least one plasticizer present in an amount of 2 to 20% by dry weight based on the total weight of the coating composition, and wherein at least one of said at least one plasticizer is selected from the group consisting of: glycerol esters, phthalates, citrates, sebacates, cetyl alcohol esters, and castor oil;
  and wherein the in vitro release profile of the suspension of microcapsules in an aqueous liquid phase on day ten is similar to the release profile on day zero, as measured using a type II apparatus according to the European Pharmacopoeia 3rd edition, in a phosphate buffer medium of pH 6.8, at a temperature of 37° C.
2. The suspension according to claim 1, wherein
  said the at least one film-forming polymer (P1) is selected from the group consisting of ethyl cellulose and cellulose acetate;
  said at least one nitrogen-containing polymer (P2) is selected from the group consisting of polyacrylamide and polyvinylpyrrolidone; and
  said at least one plasticizer is castor oil.
3. The suspension according to claim 1, wherein the film coating consists of a single layer.
4. The suspension according to claim 1, wherein said suspension comprises 30 to 95% by weight of liquid phase; and 5 to 70% by weight of microcapsules.
5. The suspension according to claim 1, wherein the proportion of dissolved amoxicillin originating from the microcapsules is less than or equal to 15% by weight of the total weight of the amoxicillin contained in the microcapsules.
6. The suspension according to claim 1, wherein the amoxicillin contained in the microcapsules saturates the liquid phase with amoxicillin.
7. The suspension according to claim 1, wherein prior to the incorporation of the microcapsules into the aqueous liquid phase, the aqueous liquid phase is at least partially saturated with amoxicillin.
8. The suspension according to claim 1 wherein the microcapsules have a particle size less than or equal to 1000 microns.
9. The suspension according to claim 1 wherein from 1 to 50% of the total weight of the coated microcapsules is film coating.
10. The suspension according to claim 1, having an in vitro release profile obtained using a type II apparatus according to the European Pharmacopoeia 3rd edition, in a phosphate buffer medium of pH 6.8 and at a temperature of 37° C., such that: the proportion PI of amoxicillin released during the first 15 minutes of the dissolution test is such that: PI≦15%; and the remaining amoxicillin is released over a period such that the release time of 50% by weight of amoxicillin ($t_{1/2}$) is defined as follows (in hours): $0.5 \leq t_{1/2} \leq 30$.
11. The suspension according to claim 1 wherein the pH of the suspension is arbitrarily acidic or neutral.
12. The suspension according to claim 1 wherein the suspension comprises at least one rheology modifier.
13. The suspension according to claim 1 wherein the suspension further comprises at least one agent for modifying the solubility of the amoxicillin in the aqueous liquid phase.
14. The suspension according to claim 1 wherein the suspension further comprises at least one additive selected from the group consisting of: surfactants, colourants, dispersants, preservatives, taste improvers, flavourings, sweeteners, antioxidants, and mixtures thereof.
15. A kit for preparing the suspension according to claim 1, wherein said kit comprises:
  microcapsules in substantially dry form comprising amoxicillin for saturating the liquid phase with amoxicillin once the solid form and liquid phase have been brought into contact;
  a mixture of microcapsules in substantially dry form containing amoxicillin in the dose that is just necessary for modified release, wherein each microcapsule comprises (a) a core comprising amoxicillin and (b) a film coating that: (i) is applied to the core, (ii) controls the modified release of the amoxicillin in gastrointestinal tract fluids, and (iii) comprises:
    (1) at least one film-forming polymer (P1) insoluble in gastrointestinal tract fluids, present in an amount of 50 to 90% by dry weight based on the total weight of the coating composition, and wherein at least one of said at least one film-forming polymer (P1) is a water-insoluble cellulose derivative;
    (2) at least one nitrogen-containing polymer (P2) present in an amount of 2 to 25% by dry weight based on the total weight of the coating composition, and wherein at least one of said at least one nitrogen-containing polymer (P2) is selected from the group consisting of: polyacrylamide, poly-N-vinylamide, and poly-N-vinyllactam; and
    (3) at least one plasticizer present in an amount of 2 to 20% by dry weight based on the total weight of the coating composition, and wherein at least one of said at least one plasticizer is selected from the group consisting of: glycerol esters, phthalates, citrates, sebacates, cetyl alcohol esters, and castor oil;
  and wherein the in vitro release profile of the suspension of microcapsules in an aqueous liquid phase on day ten is similar to the release profile on day zero, as measured using a type II apparatus according to the European

Pharmacopoeia 3rd edition, in a phosphate buffer medium of pH 6.8, at a temperature of 37° C.; together with immediate-release uncoated amoxicillin in a necessary and sufficient dose to saturate the liquid phase with amoxicillin once the saturation dose of amoxicillin and the liquid phase have been brought into contact;

the liquid phase;

at least part of the ingredients useful for its preparation;

the protocol for preparation of the suspension; or combinations thereof.

16. The suspension according to claim 1, wherein said film coating further comprises at least one surfactant or lubricant present in an amount of 2 to 20% by dry weight based on the total weight of the coating composition, and wherein at least one of said at least one surfactant or lubricant is selected from the group consisting of: anionic surfactants, non-ionic surfactants, and lubricants, and mixtures thereof.

17. The suspension according to claim 16, wherein at least one of the at least one surfactant or lubricant is selected from the group consisting of: an alkali metal of fatty acids, an alkaline earth metal salt of fatty acids, stearic acid, oleic acid, a polyethoxylated sorbitan ester, a polyethoxylated castor oil derivative, a stearate, stearylfumarate, sodium stearylfumarate, glycerol behenate.

18. The suspension according to claim 4, wherein said suspension comprises 60 to 85% by weight of liquid phase.

19. The suspension according to claim 4, wherein said suspension comprises 15 to 40% by weight of microcapsules.

20. The suspension according to claim 1, wherein the proportion of dissolved amoxicillin originating from the microcapsules is less than or equal to 5% by weight of the total weight of amoxicillin contained in the microcapsules.

21. The suspension according to claim 1 wherein the microcapsules have a particle size of between 200 and 800 microns.

22. The suspension according to claim 1 wherein the microcapsules have a particle size of between 200 and 600 microns.

23. The suspension according to claim 1 wherein from 5 to 40% of the total weight of the coated microcapsules is film coating.

24. The suspension according to claim 10, wherein the proportion PI of amoxicillin released during the first 15 minutes of the dissolution test is such that: $PI \leq 5\%$ and the remaining amoxicillin is released over a period such that the release time of 50% by weight of AP ($t_{1/2}$) is defined as follows (in hours): $0.5 \leq t_{1/2} \leq 20$.

* * * * *